United States Patent
Geist et al.

(10) Patent No.: US 12,402,895 B2
(45) Date of Patent: Sep. 2, 2025

(54) SURGICAL GUIDE AND FIXATION INSERTION DEVICE

(71) Applicant: INTEGRITY IMPLANTS INC., Palm Beach Gardens, FL (US)

(72) Inventors: Wyatt Drake Geist, Davie, FL (US); John Souza, Monroe, NC (US)

(73) Assignee: INTEGRITY IMPLANTS INC., Palm Beach Gardens, FL (US)

( * ) Notice: Subject to any disclaimer, the term of this patent is extended or adjusted under 35 U.S.C. 154(b) by 244 days.

(21) Appl. No.: 18/134,007

(22) Filed: Apr. 12, 2023

(65) Prior Publication Data

US 2023/0355250 A1 Nov. 9, 2023

Related U.S. Application Data

(60) Provisional application No. 63/428,713, filed on Nov. 29, 2022, provisional application No. 63/330,224, filed on Apr. 12, 2022.

(51) Int. Cl.
*A61B 17/16* (2006.01)
*A61B 17/86* (2006.01)

(52) U.S. Cl.
CPC ...... *A61B 17/1624* (2013.01); *A61B 17/1633* (2013.01); *A61B 17/1671* (2013.01); *A61B 17/862* (2013.01); *A61B 17/1628* (2013.01); *A61B 17/1631* (2013.01)

(58) Field of Classification Search
CPC .......................... A61B 17/8875; A61B 17/8897
USPC ........................................................ 606/104
See application file for complete search history.

(56) References Cited

U.S. PATENT DOCUMENTS

| | | | |
|---|---|---|---|
| 2014/0276892 A1 | 9/2014 | Pakzaban et al. | |
| 2015/0351820 A1* | 12/2015 | Straslicka | A61B 17/1697 606/169 |
| 2017/0340374 A1* | 11/2017 | Xie | A61B 17/8897 |
| 2018/0185080 A1* | 7/2018 | Bosshard | A61B 17/8861 |
| 2019/0343568 A1* | 11/2019 | Childers | A61B 17/1697 |
| 2020/0197064 A1 | 6/2020 | Geist et al. | |
| 2020/0305944 A1 | 10/2020 | Geist et al. | |
| 2022/0142681 A1* | 5/2022 | Jeffords | A61B 17/7091 |

OTHER PUBLICATIONS

International Search Report issued to corresponding PCT Application No. PCT/us2023/018391 dated Jul. 5, 2023.

* cited by examiner

*Primary Examiner* — Matthew J Lawson
(74) *Attorney, Agent, or Firm* — McNees Wallace & Nurick LLC (57) ABSTRACT

A surgical guidance device is cannulated for passage of a guidewire or pin and includes a hand grip and differential control assembly for driving the guidewire or pin and differentially driving a screw, such as but not limited to a pedicle screw, into bone. The differential control assembly resides in a housing, and includes a differential control assembly for gripping and locking or releasing the guidewire or pin and effecting directional movement (relative to the user holding the surgical guidance device) either distally into the bone or proximally away from bone to thereby drive or retract the guidewire. The differential control assembly also allows distal or proximal drive of a screw, such that one or both the guidewire and screw can be passed proximally or distally alone or together.

20 Claims, 7 Drawing Sheets

SURGICAL GUIDE AND FIXATION INSERTION DEVICE

RELATED APPLICATIONS

This application claims the benefit of and priority to U.S. provisional application No. 63/428,713 filed Nov. 29, 2022, and U.S. provisional application No. 63/330,224 filed Apr. 12, 2022, which are hereby incorporated herein by reference in their entireties.

FIELD OF THE INVENTION

The invention relates to a surgical guidance device and system and a method for use of the surgical guidance device for surgical spinal procedures. In particular, the surgical guidance device includes a driving tool and differential drive system for inserting and positioning, sequentially, a guidewire and a screw into bone, in particular for inserting a cannulated pedicle screw into a vertebra over a guidewire.

BACKGROUND OF THE INVENTION

Medical procedures calling for the placement of a screw or other fixation implant within bone often rely upon initial placement of a guide, such as a pin or a guidewire, over which the screw or implant is guided for insertion within bone. In some examples, medical procedures involving the vertebrae can be particularly complicated because of the precision and accuracy required to avoid both neural damage and injury to major blood vessels when placing the guide and then driving the implant into bone. Precision depth guided devices may be employed for such applications, in particular when the mode of surgical access is percutaneous. In the context of spine surgeries, the surgical technique typically involves penetration of the hard cortical bone of the vertebra then traversal of the softer cancellous bone lying thereunder. A concomitantly greater force is typically required to penetrate the cortical bone as compared to the force needed for passage through the underlying cancellous bone. Careful control of the forces and depth of penetration of the guide and the implant are essential to avoid damage to the spinal cord and/or other organs or blood vessels located adjacent the spine. Current solutions for placement of guidewires and pins and subsequent placement of screws rely on various manually or power driven penetration which suffer from limited control to avoid tissue damage.

There remains a need in the art for a device and system and method that enables precise and differentially controlled insertion of the guidewire and screw, and in particular for precisely controlling the depth that the guidewire can penetrate. The guidance device, system and method should also be constructed to allow the user to precisely retract the guidewire through bone as needed.

SUMMARY

In various embodiments, the disclosure provides a surgical guidance device 10, system and method for forming a pilot bore and passing a guidewire (or pin) 15 into bone based on a trajectory established using radiography (for example, but not limited to, 2D or 3D fluoroscopy or CT).

The surgical guidance device 10 is cannulated for passage of a guidewire or pin and includes a hand grip 40 and differential control assembly 50 for driving the guidewire 15 (or pin) and differentially driving a screw, such as but not limited to a pedicle screw, into bone. The differential control assembly 50 resides in a housing 20, and includes a differential control assembly 50 for gripping and locking or releasing the guidewire 15 and effecting directional movement (relative to the user holding the surgical guidance device 10) either distally into the bone or proximally away from bone to thereby drive or retract the guidewire. The differential control assembly 50 also allows distal or proximal drive of a screw, such that one or both the guidewire and screw can be passed proximally or distally alone or together.

One key functional feature of the surgical guidance device 10 is the ability to establish a preselected depth limit on the passage of the guidewire or pin whereupon the surgical guidance device 10 can be activated passively by means of a positive stop feature, or by user actuation to lock the guidewire or pian and prevent further distal advancement of the guidewire 15 or pin, and the device can be further actuated to actively withdraw the guidewire 15 and isolate its movement while directing movement of only a screw. Accordingly, the device prevents passage of a guidewire or pin farther into bone than the preselected depth limit and operates to withdraw the guidewire or pin without affecting the placement of a screw.

In an exemplary embodiment, the surgical guidance device 10 includes
  a differential control assembly 50 that is cannulated for passage of a guidewire 15 therethrough, and aligned along a common axis with and within a housing 20, the differential control assembly 50 including a support shaft 51 having a proximally positioned drive connector 59 for engagement with a powered driving device, and a distally positioned tool connector 52 configured for attachment of a driver tool guide 200, a screw gear 53 and a chuck 54 that are releasably engagable to direct rotational movement of the screw gear 53 when the chuck 54 is engaged therewith, and a threaded carriage 55 translatable along the support shaft 51 for directing proximal or distal movement of the guidewire 15 through the differential control assembly 50, the threaded carriage 55 including at least one positive stop 57 which limits the proximal and distal translation of the carriage 55 within the housing 20, and
  an actuator assembly 29 including a handle 42 operably attached to a chuck mover 43 for actuating engagement of the chuck 54 with the screw gear 53, a directional actuator 30 for actuating movement of the carriage 55 proximally or distally, and a carriage lock 31 configured to releasably engage a thread guide 32 with the threaded carriage 55 wherein engagement thereof permits proximal or distal movement of the threaded carriage 55 along the support shaft 51 to effect proximal or distal movement of the guidewire 15,
  wherein the differential control assembly 50 is actuatable to first drive the guidewire 15 into a target site by engagement of the carriage lock 31 with the carriage 55 to direct distal movement of the guidewire 15, the depth thereof being governed by the at least one positive stop 57, and to differentially drive a screw affixed to the surgical guidance device 10 by actuating the handle 42 to engage the chuck 54 with the screw gear 53.

In an embodiment, the surgical guidance device 10 includes
  a housing 20 having a proximal end 21, a center drive barrel 24, and a distal end 22, the proximal end 21 adapted with a hand grip 40 for gripping the surgical guidance device 10, the center drive barrel 24 configured to contain a differential control assembly 50 housed therein, the proximal end 21 of the housing 20 adapted for securing the housing to a powered driving device such as a drill or power drill, the differential control assembly 50 being cannulated for passage of a guidewire therethrough, and aligned along a common axis with and within the housing 20, the differential control assembly 50 including a support shaft 51 having a proximally positioned drive connector 59 for engagement with the powered driving device, and a distally positioned tool connector 52 configured for attachment of a driver tool guide 200, a screw gear 53 and a chuck 54 that are releasably engagable to direct rotational movement of the screw gear 53 when the chuck 54 is engaged therewith, a threaded carriage 55 translatable along the support shaft 51 for directing proximal or distal movement of the guidewire 15 through the differential control assembly 50, the threaded carriage 55 including at least one positive stop 57 which limits the proximal and distal translation of the carriage 55 within the housing 20, and an actuator assembly 29 including a hand grip 40 including a handle 42 operably attached to a chuck mover 43 for actuating engagement of the chuck 54 with the screw gear 53, a directional actuator 30 for actuating movement of the carriage 55 proximally or distally, and a carriage lock 31 configured to releasably engage a thread guide 32 with the threaded carriage 55 wherein engagement thereof permits proximal or distal movement of the threaded carriage 55 along the support shaft 51 to effect proximal or distal movement of the guidewire 15, wherein the differential control assembly 50 is actuatable to first drive the guidewire 15 into a target site by engagement of the carriage lock 31 with the carriage 55 to direct distal movement of the guidewire 15, the depth thereof being governed by the at least one positive stop 57, and to differentially drive a screw affixed to the surgical guidance device 10 by actuating the handle 42 to engage the chuck 54 with the screw gear 53.

In some embodiments, the surgical guidance device 10 includes a fixed grip 41.

In some embodiments, the driver tool 200 includes a drill guide.

In some embodiments, the differential control assembly 50 includes a connector 51 for securing to a powered driving device such as a drill or power drill.

In some embodiments, the surgical guidance device 10 includes a trigger 70 for disengaging the screw gear 53 to stop rotation of a screw affixed to the surgical guidance device 10.

In some embodiments, the surgical guidance device 10 includes a guidewire lock 71 for locking the guidewire in place to prevent one or more of its rotation, proximal translation, distal translation, or a combination thereof.

In some embodiments, the driver tool 200 is constructed to cooperate with a conjugately shaped portion of a screw and is adapted to receive passage of the guidewire therethrough.

In some embodiments, the directional actuator 30 is actuated to direct the guidewire 15 to move distally, and is released to retract the guidewire to move proximally, wherein displacement of the guidewire 15 is governed by the at least one positive stop 57, and wherein retraction of the guidewire 15 with the directional actuator 30 thereby differently permits distally directed driving of only the screw gear 53.

In some embodiments, the guidewire 15 is constructed from a material having sufficient column strength for penetrating a bone.

In some embodiments, the surgical guidance device 10 has a fixed length from proximal to distal wherein rotation and translation of the differential control assembly 50 occurs within the housing 20.

In some embodiments, the proximal end of the housing 20 is integral with a powered driving device 500.

In some embodiments, the at least one positive stop is at least one ring that interferes within the housing to limit movement of the carriage 55.

In some embodiments, at least one positive stop includes two or more rings oriented proximally and distally relative to the carriage 55.

In some embodiments, the positive stop is a sleeve that encloses the carriage 55 to thereby limit its translation.

In an embodiment, the invention includes a method for directing sequentially a guidewire 15 and a screw into target bone by differentially directing the placement of a guidewire into bone and thereupon preventing further displacement of the guidewire 15 into bone and thereafter introducing the screw into bone, wherein the guidewire 15 is either maintained in place within the bone, or is withdrawn before or as the screw is inserted into the bone.

DESCRIPTION OF THE DRAWINGS

The features and advantages of the general inventive concepts will become apparent from the accompanying drawings which depict various alternate embodiments of the surgical guidance device and method. The drawings illustrate various embodiments of the present invention and methods by which they may be assembled and operated. Like reference numerals refer to like components in the various figures.

FIG. 9 is a schematic showing in a vertical orientation a side view portion of an embodiment of a differential control assembly of the surgical guidance device, the depicted differential control assembly connectable at its proximal (top) end to a drill, including a screwdriver sleeve with locking pin, and a carriage including a driving chuck, with pin notches region and stops and a washer to limit proximal to distal motion the assembly having a guidewire passed through;

FIG. 11 is a schematic showing a guidance device including a proximal handle (right) engaged or engagable with a drill, a trigger connected to a differential control assembly as shown in FIG. 9 and FIG. 10, and a distal driver in a vertical orientation a portion of a differential control assembly with a guidewire passed through;

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DESCRIPTION

In various embodiments, the invention provides an integrated, all-in-one powered device that can deploy a guidewire or pin, for example a surgical K-wire, or a screw or other fixator, such as a pedicle screw, or both. The surgical guidance device 10 is adapted to be attached to a conventional drill, or may be integrated into a drill device, or may have integrated onboard power for driving, as shown in alternate embodiments herein.

The surgical guidance device 10 is cannulated for passage of a guidewire or pin and includes a hand grip 40 and differential control assembly 50 for driving the guidewire 15 or pin and differentially driving a screw, such as but not limited to a pedicle screw, into bone. The differential control assembly 50 resides in a housing 20, and includes a differential control assembly 50 for gripping and locking or releasing the guidewire or pin and effecting directional movement (relative to the user holding the surgical guidance device 10) either distally guidewire or pin into the bone or proximally away from bone to thereby drive or retract the guidewire. The differential control assembly 50 also allows distal or proximal drive of a screw, such that one or both the guidewire and screw can be passed proximally or distally alone or together.

One key functional feature of the surgical guidance device 10 is the ability to establish a preselected depth limit on the passage of the guidewire or pin whereupon the surgical guidance device 10 can be activated passively by means of a positive stop feature, or by user actuation to lock the guidewire or pian and prevent further distal advancement of the guidewire 15 or pin, and the device can be further actuated to actively withdraw the guidewire 15 or pin and isolate its movement while directing movement of only a screw. Accordingly, the device prevents passage of a guidewire or pin farther into bone than the preselected depth limit and operates to withdraw the guidewire or pin without affecting the placement of a screw.

In an exemplary embodiment, the surgical guidance device 10 includes a differential control assembly 50 that is cannulated for passage of a guidewire 15 therethrough, and aligned along a common axis with and within a housing 20, the differential control assembly 50 including a support shaft 51 having a proximally positioned drive connector 59 for engagement with a powered driving device, and a distally positioned tool connector 52 configured for attachment of a driver tool guide 200, a screw gear 53 and a chuck 54 that are releasably engagable to direct rotational movement of the screw gear 53 when the chuck 54 is engaged therewith, and a threaded carriage 55 translatable along the support shaft 51 for directing proximal or distal movement of the guidewire 15 through the differential control assembly 50, the threaded carriage 55 including at least one positive stop 57 which limits the proximal and distal translation of the carriage 55 within the housing 20, and a actuator assembly 29 including a handle 42 operably attached to a chuck mover 43 for actuating engagement of the chuck 54 with the screw gear 53, a directional actuator 30 for actuating movement of the carriage 55 proximally or distally, and a carriage lock 31 configured to releasably engage a thread guide 32 with the threaded carriage 55 wherein engagement thereof permits proximal or distal movement of the threaded carriage 55 along the support shaft 51 to effect proximal or distal movement of the guidewire 15. The differential control assembly 50 is actuatable to first drive the guidewire 15 into a target site by engagement of the carriage lock 31 with the carriage 55 to direct distal movement of the guidewire 15, the depth thereof being governed by the at least one positive stop 57, and to differentially drive a screw affixed to the surgical guidance device 10 by actuating the handle 42 to engage the chuck 54 with the screw gear 53.

The guidewire can be a surgical K-wire or a pin or other internal guiding pin like device. Power may direct pin motion in a distal or proximal direction by rotating or malleating and would rotate the screw upon engagement of the chuck 54 with the screw gear 53. In some embodiments, the surgical guidance device 10 is particularly adapted to differentially drive the guidewire, the screw or both, and may drive the screw distally while withdrawing the guidewire proximally.

Thus, in some embodiments, the surgical guidance device 10 drives only the guidewire and holds the screw static, or drives only the screw holding the guidewire static, or drives the screw either proximally or distally while withdrawing the guidewire proximally (i.e., withdrawing from the bone). The invention this thus advantageous as compared to existing solutions which rely on separately actuated pin and screw advancement/withdrawal, and further may rely solely on manual driving without power.

Referring now to the drawings as variously depicted in FIG. 1-FIG. 20, various embodiments and configurations of the surgical guidance device 10 are shown.

Figure 1:
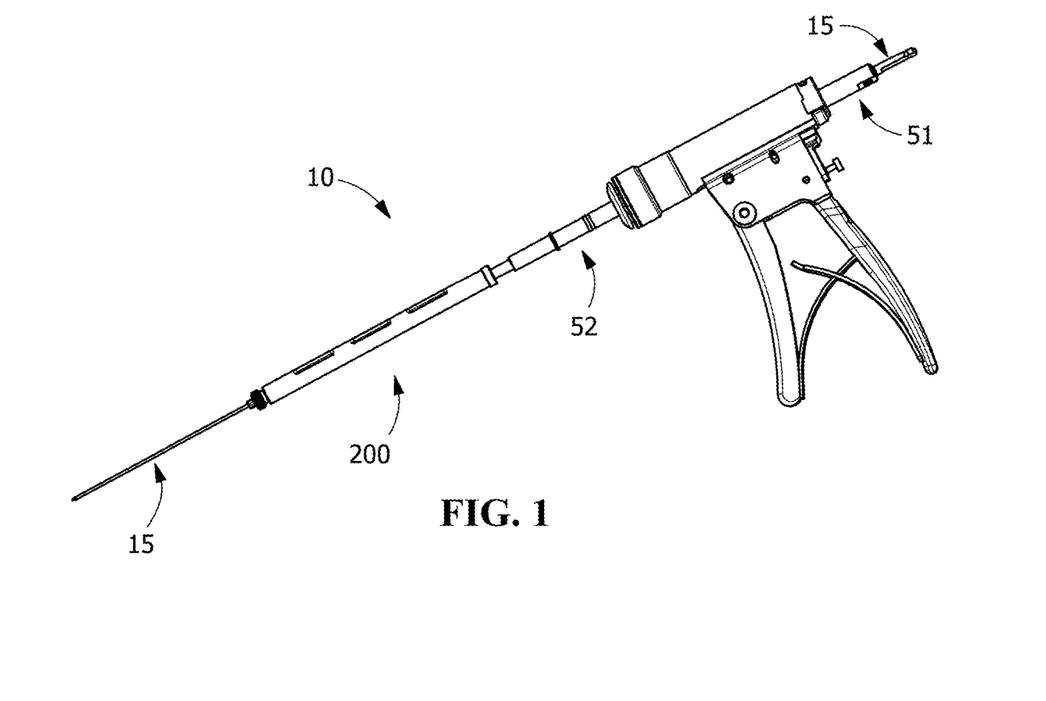
FIG. 1 is a side perspective view schematic of a first embodiment of the surgical guidance device according to the disclosure.
Figure 2:
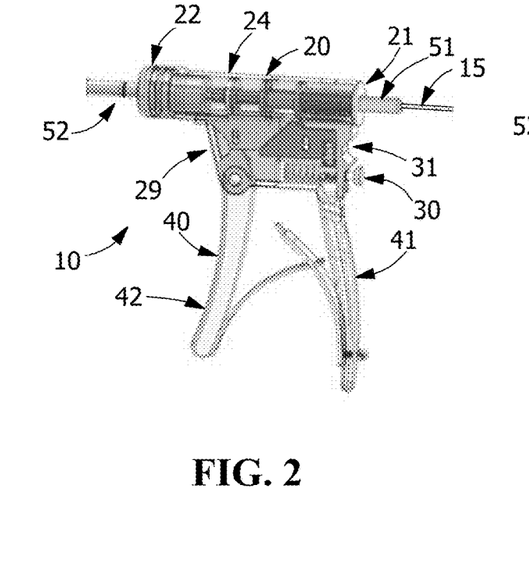
FIG. 2 is partial side perspective view schematic of the embodiment of the surgical guidance device shown in FIG. 1 wherein the surgical guidance device is shown with a guidewire passed through its central cannulation and in the included differential control assembly embodiment thereof is in a neutral position.
Figure 3:
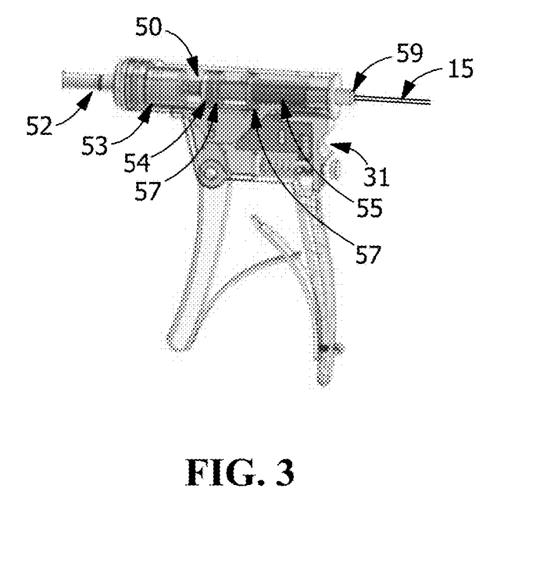
FIG. 3 is partial side perspective view schematic of the embodiment of the surgical guidance device shown in FIG. 1-FIG. 2 wherein the surgical guidance device is shown with a guidewire passed through its central cannulation and retracted toward the proximal (right side) end of the surgical guidance device.
Figure 4:
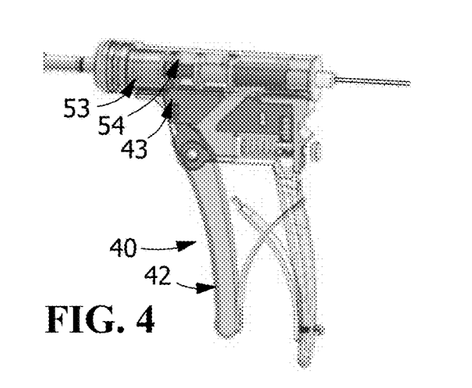
FIG. 4 is partial side perspective view schematic of the embodiment of the surgical guidance device shown in FIG. 1-FIG. 3 wherein each of the chuck mover and the directional actuator are actuated to direct distal movement of the screw gear and proximal movement of the guidewire.
Figure 5:
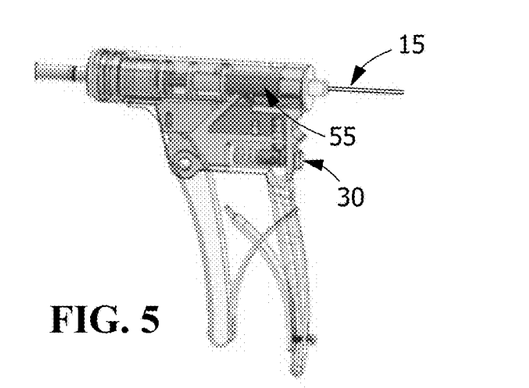
FIG. 5 is partial side perspective view schematic of the embodiment of the surgical guidance device shown in FIG. 1-FIG. 4 wherein the guidewire is locked.
Figure 6:
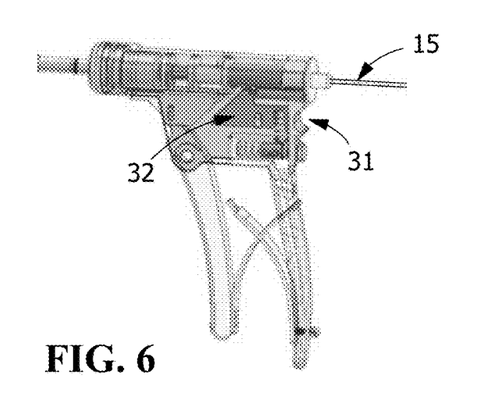
FIG. 6 is partial side perspective view schematic of the embodiment of the surgical guidance device shown in FIG. 1-FIG. 5 wherein the threaded carriage is engaged prior to actuation of the carriage lock.
Figure 7:
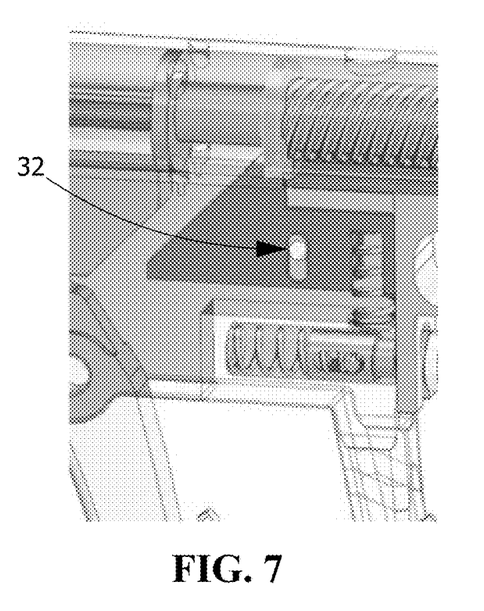
FIG. 7 is a close-up, side perspective view schematic of the carriage lock mechanism as shown in FIG. 1-FIG. 6.
Figure 8:
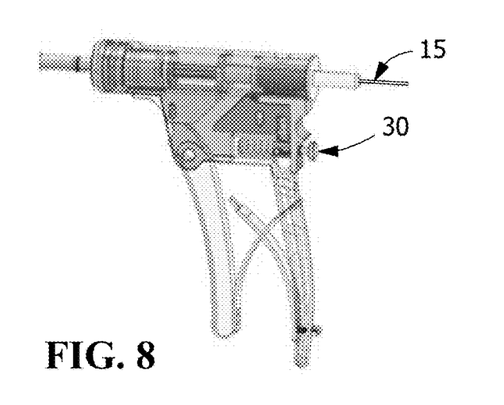
FIG. 8 is a is partial side perspective view schematic of the embodiment of the surgical guidance device shown in FIG. 1-FIG. 7 wherein the threaded carriage is disengaged by actuation of the carriage lock.
Figure 9:
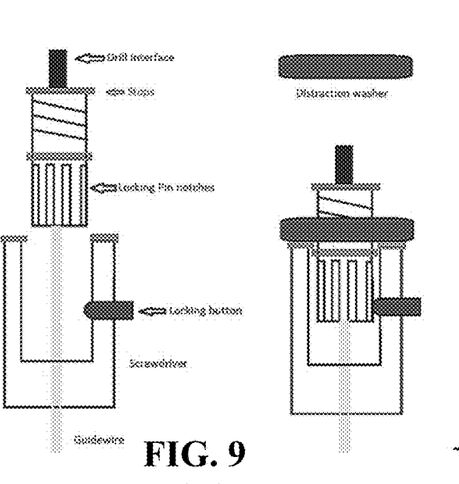

Referring now to FIGS. 1-8, an embodiment of the surgical guidance device 10 is shown in which the surgical guidance device 10 is shown in FIG. 2-8 in series from initial assembly with the guidewire 15 passed through the cannula in the differential control assembly 50, through to engagement driver tool guide 200 (tool not shown), for example, in FIG. 8, wherein an housing 20 is shown as transparent, and the internal differential control assembly 50 are shown through the transparent housing 20. As shown in FIG. 8, within the housing are a carriage with stops/sleeve, chuck for driving the screwdriver, and screw gear components.

Figure 10:
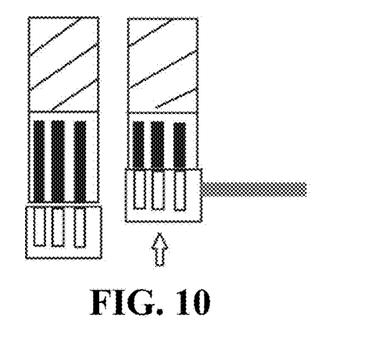
FIG. 10 is a schematic showing in a vertical orientation a driving chuck portion of a differential control assembly with a guidewire passed through and a locking tray to lock rotation of the driving chuck.
Figure 11:
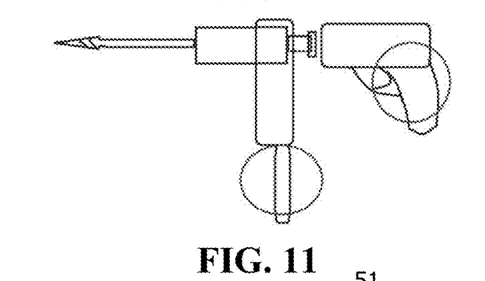
Figure 12:
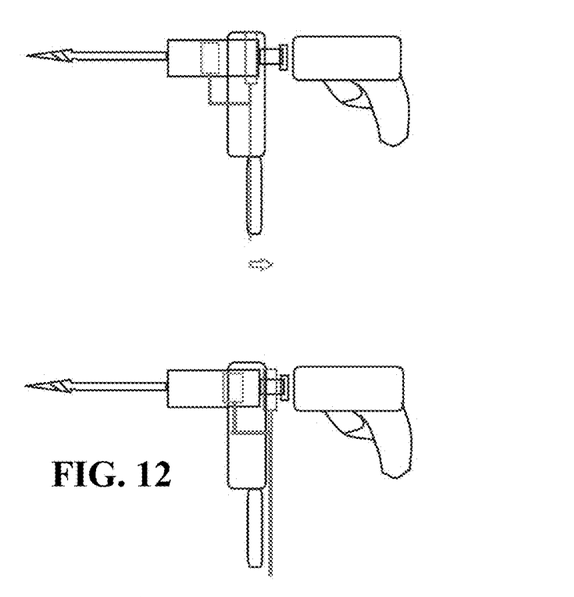
FIG. 12 is a schematic showing in two views the guidance device shown in FIG. 11 wherein movement of the trigger from distal to proximal directs engagement of the driving chuck to permit driving of one of a screw or a guidewire.
Figure 13:
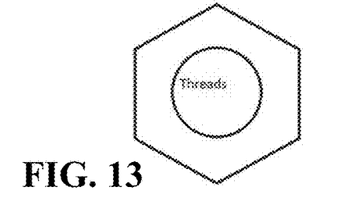
FIG. 13 is a top view of an embodiment of the washer having interior threads for engaging a threaded portion of the carriage.

Referring again to the drawings as specifically depicted in FIG. 9-FIG. 13, an embodiment of a differential control assembly 50 is shown in which the guidewire 15 is advanced by actuation of the surgical guidance device 10 while the screwdriver component is disengaged from power. In a representative example, the guidewire 15 may be advanced by a fixed distance, for example for total length of 10 mm upon reaching this distance, the carriage hit a stop. Upon reaching the stop, an actuator, such as a button, as shown in FIG. 10, is actuated to allow the drill to engage to start driving the screw. Referring to FIG. 12, an optional locking button is a tray is introduced from below.

In various embodiments, it will be appreciated that any predetermined depth of travel of the guidewire, forward or backward, alone or together with the screw, may be selected from 0-50 mm, or from 5-30 mm, or from 10-20 mm, or 15 mm, or any other range or increment.

Figure 14:
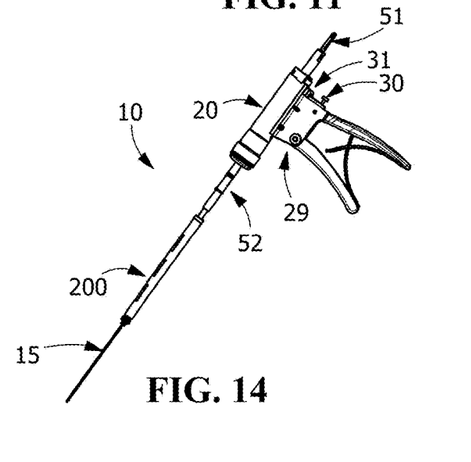
FIG. 14 is a side perspective schematic view of a second embodiment of the surgical guidance device according to the disclosure.
Figure 15:
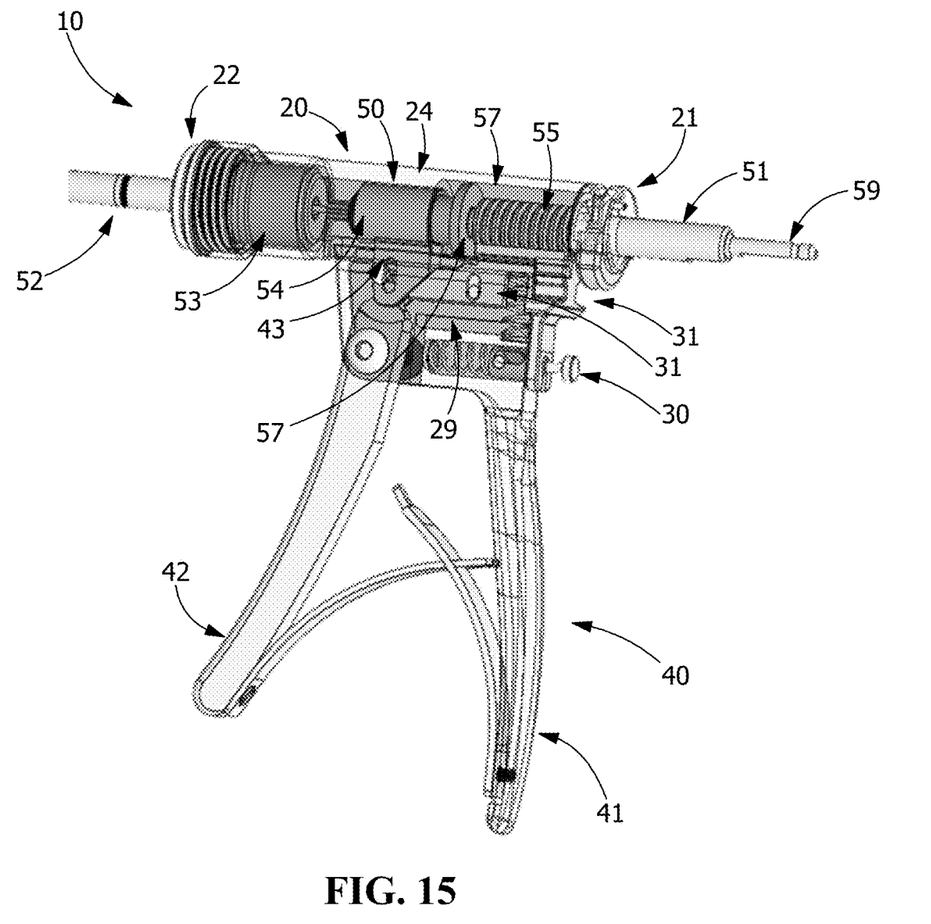
FIG. 15 includes a photographic image of a physical embodiment of the depicting the surgical guidance device shown in FIG. 14, and a partial side perspective view schematic of the embodiment of the surgical guidance device shown in FIG. 14 wherein the surgical guidance device is shown with a guidewire passed through its central cannulation.

Referring again to the drawings as specifically depicted in FIG. 14-FIG. 15, the surgical guidance device 10 is shown, wherein an outer housing is shown as transparent, and the internal differential control assembly 50 are shown through the transparent housing 20. In this embodiment, a locking button 71 for securing and thereby preventing movement of the guidewire is positioned at the proximal end of the housing/carriage.

In some embodiments, the surgical guidance device 10 will either have a fixed stop to prevent translation of the carriage or the carriage or the stop is adjustable to allow for adjustable guidewire displacement.

In some embodiments, the carriage will freely float proximal and distal along the differential control assembly 50 lacking the at least one stop.

Referring again to FIG. 9-13, in some embodiments, such as shown in FIG. 9-13, the stop may be an adjustably positionable washer, or a locking pin for engaging with locking pin notches, or a sleeve.

Referring again to FIG. 9-13, in some embodiments, the carriage can be rotationally locked into the screwdriver by engaging the locking pin or pins into the locking grooves. In some embodiments, the groves allow for the carriage to displace rotational power, but still allow for proximal and distal translation along the differential control assembly 50. In some embodiments, the distraction washer is adjustable and stops the depth the guidewire can be driven. When the washer is rotated it can either permit a greater length of guidewire to advance distally, or retract the guidewire. In some embodiments, the distraction washer has a reverse thread, so after the locking button is pushed, the user's hand is removed from the screwdriver and placed on the distraction washer. In some embodiments, when the drill is turned on the screw will drive and the carriage will be pulled back in relation to the screwdriver. Thus, in such embodiments, the effect is to retract the guidewire 15.

More generally, in those embodiments including a sleeve or stop, the surgical guidance device 10 is operated such that the sleeve or stop interacts with or without a distraction washer. In the instance of a distraction washer, the washer contacting the sleeve is forced to spin towards the screwdriver. Once the washer hits the screwdriver it will back up the guidewire 15. To avoid premature withdrawal of the guidewire, a selected length of tread, for example, 10 mm ensures that if the screw isn't advanced into the bone upon engagement of the driver, the guidewire 15 is maintained in place until the screw is advanced the selected distance. The handle as controlled by the user to maneuver the sleeve to interact with the washer at the same time the lock is engaged with the screwdriver handle.

In various embodiments, in use, the distal end of the surgical guidance device 10 is docked, with the screw in direct contact on bone, for example in a representative spinal surgery, on the Pars interarticularis, which is the small segment of bone that joins the facet joints in the back of the spine.

Upon engagement of the screwdriver, the screw is driven, for example for a distance of about 10 mm. In some embodiments the guidewire 15 length maintained at 10 mm. Preservation of the guidewire 15 placement in bone is beneficial in the instance where initial purchase of the screw tip in bone is not established, thus ensuring that the trajectory is not lost. In other conventional approaches, early withdrawal of the guidewire 15 prior to engagement of the screw in bone can require extensive additional steps including additional radiographic shots in order to reestablish wire placement in bone. As the screw is driven further into the bone, the guidewire 15 may be retracted either by automated actuation or by user actuation. For example, the locking button is depressed releasing the guidewire 15 to enable its retraction. Thus, the further additional depth screw is driven, the guidewire 15 starts retracting, in some examples, within 10 additional mm.

It will be appreciated that while the embodiments herein include a differential control assembly 50 having various differences in their components, the embodiments may be modified to include any of the differential control assembly 50 components and actuators as described herein. For example, some or all of the features of the embodiment of a differential control assembly 50 as specifically depicted in FIG. 9-FIG. 13 may be incorporated in a surgical guidance device 10 according to the disclosure.

Referring again to the drawings, FIG. 14 shows an embodiment of the surgical guidance device 10 which differs in some respects from the embodiment shown in FIG. 1-8, and FIG. 15 shows the embodiment of FIG. 14 including a photographic image of a prototype of the surgical guidance device 10 showing engagement with a drill on the proximal end, and at the distal end, a pedicle screw with affixed tulip head is attached to the distal end of the driver via a locking nut, and the drive is in turn affixed to the surgical guidance device 10 above the locking nut. FIG. 15 also shows a partial view of the surgical guidance device 10 with transparent rendering of the housing 20 to show the differential control assembly 50.

Figure 16:
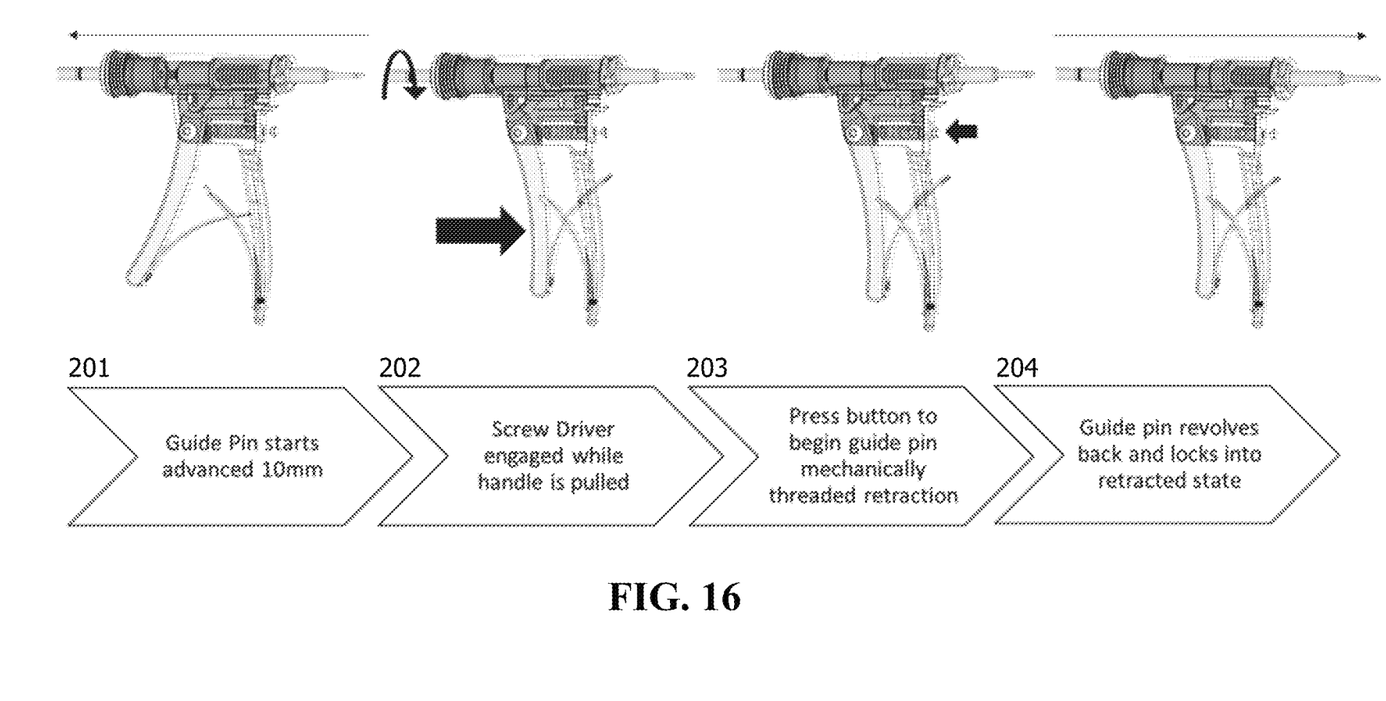
FIG. 16 is schematic showing sequential images of the embodiment of the surgical guidance device shown in FIG. 14-15, each image including corresponding flow diagram descriptions of the actuation of features of the device.

Referring now to FIG. 16 a schematic shows sequential images of the embodiment of the surgical guidance device shown in FIG. 14-15, each image including corresponding flow diagram descriptions of the actuation of features of the device. FIG. 16 provides a stepwise guide to actuation of the surgical guidance device 10 consistent with the above described methods of its use, whereby the surgical guidance device 10 under power, for example from a conventional drill, enables insertion of a guidewire followed by insertion of a screw and removal of the guidewire without the need for any other devices.

Figure 17:
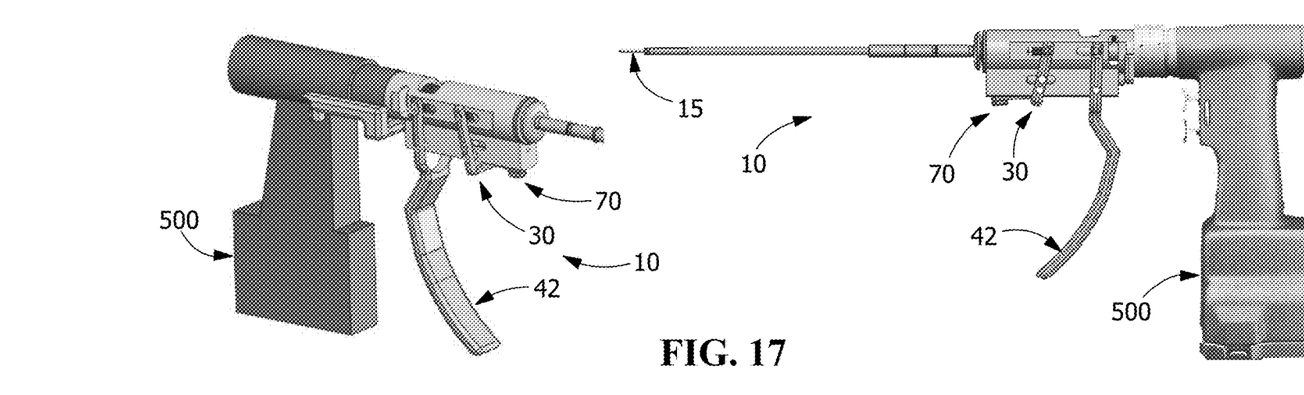
FIG. 17 is a side perspective schematic view and a side schematic view of a third embodiment of the surgical guidance device according to the disclosure.
Figure 18:
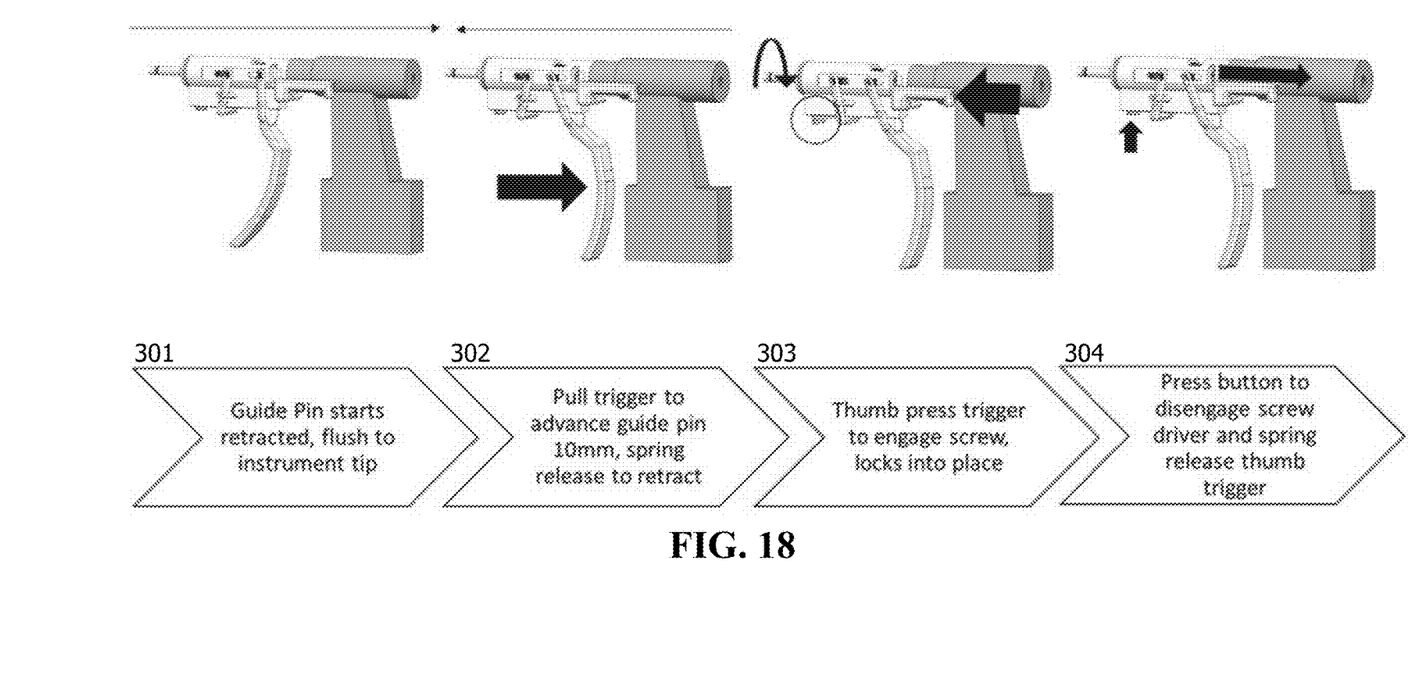
FIG. 18 is schematic showing sequential images of the embodiment of the surgical guidance device shown in FIG. 17, each image including corresponding flow diagram descriptions of the actuation of features of the device

Referring again to the drawings, FIG. 17-FIG. 18 shows an alternate embodiment of the surgical guidance device 10 which includes a fully integrated power drill that enables single handed control. FIG. 18 is schematic showing sequential images of the embodiment of the surgical guidance device shown in FIG. 17, each image including corresponding flow diagram descriptions of the actuation of features of the device, and provides a stepwise guide to actuation of the surgical guidance device 10 consistent with the above described methods of its use, whereby the surgical guidance device 10 under power, for example from a conventional drill, enables insertion of a guidewire followed by insertion of a screw and removal of the guidewire without the need for any other devices.

The embodiment shown in FIG. 1-FIG. 23 can be used by a single operate using two hands, one to control and actuate the surgical guidance device 10, and one to actuate the drill.

Figure 19:
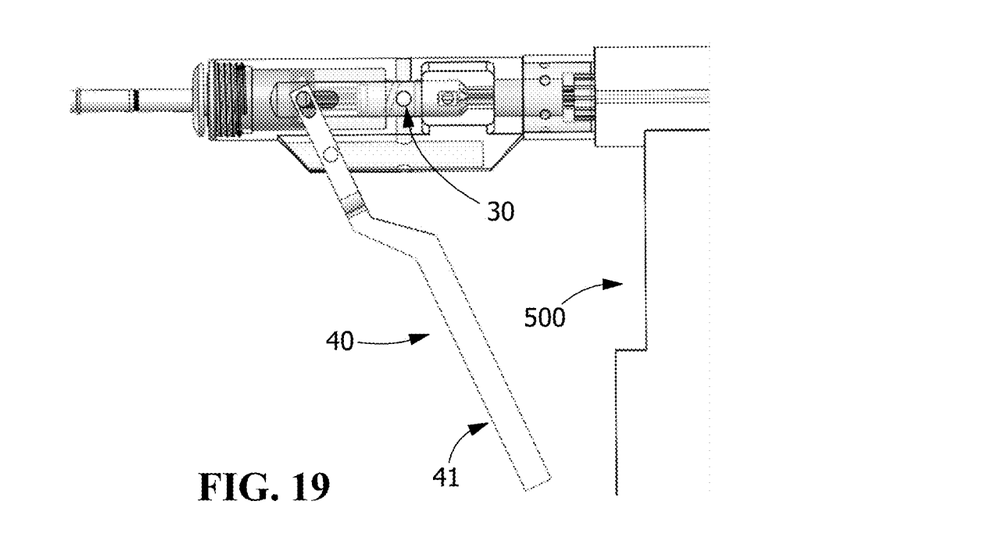
FIG. 19 is a side perspective schematic view of a fourth embodiment of the surgical guidance device according to the disclosure.

Referring again to the drawings, FIG. 19 shows yet another embodiment of the surgical guidance device 10 with further streamlined controls for single handed use, and adapted with a push button mechanism directional actuator 30 for retraction of the guidewire once acceptable screw depth has been achieved.

Figure 20:
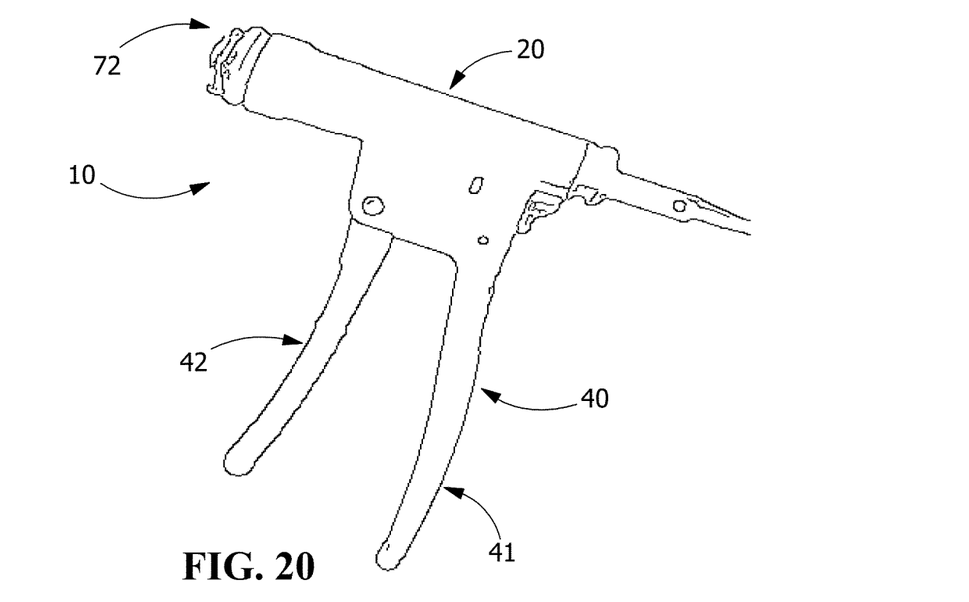
FIG. 20 is a side perspective schematic view of a fifth embodiment of the surgical guidance device according to the disclosure.

And FIG. 20 shows yet another embodiment of the surgical guidance device 10, wherein the device includes a simple push driver button 72 at its distal end to drive insertion of a guidewire.

In some embodiments, the present device 10 may be utilized for any of a variety of surgical procedures where precision of placement and control of at least a guidewire with or without a screw is needed, for example in soft tissue procedures for placement of instruments and or biopsies or removal of tissues, and in orthopedic procedures outside the spine for example in long bones, and joints including the shoulder, hip, knee or other joint.

PARTS IST surgical guidance device 10
differential control assembly 50
guide wire 15
housing 20
support shaft 51
proximally positioned drive connector 59
distally positioned tool connector 52
driver tool guide 200
screw gear 53
chuck 54
threaded carriage 55
at least one positive stop
actuator assembly 29
handle 42
chuck mover 43
directional actuator 30
carriage lock 31
thread guide 32
fixed grip 41.
trigger 70
wire lock 71
push driver button 72
screw 300
power drill 500

This description describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

The general inventive concepts will now be described with occasional reference to the exemplary embodiments of the invention. Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts.

As used herein, the singular forms "a," "an," and "the" are intended to include the plural forms as well, unless the context clearly indicates otherwise.

Unless otherwise indicated, all numbers expressing quantities, properties, and so forth as used in the specification and claims are to be understood as being modified in all instances by the term "about." Accordingly, unless otherwise indicated, the numerical properties set forth in the specification and claims are approximations that may vary depending on the suitable properties desired in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

The term "proximal" as used in connection with any object refers to the portion of the object that is closest to the operator of the object (or some other stated reference point), and the term "distal" refers to the portion of the object that is farthest from the operator of the object (or some other stated reference point). The term "operator" means and refers to any professional or paraprofessional who delivers clinical care to a medical patient, particularly in connection with the delivery of care. A "clinical subject" refers to a human or other animal who is the subject of treatment with a bone fixation or reduction device in accordance with the disclosure. With respect to any references herein that may be made relative to a clinical subject, the term "medial" indicates a direction toward the centerline axis (e.g., the spine) of the clinical subject, and the term "lateral" indicates a direction toward a side of the clinical subject. The term "system" refers to any combination of two or more of objects, devices, or components. And the term "method" refers to any one of methods of using a device or system, and surgical methods or techniques employing a device or system.

While various inventive aspects, concepts, and features of the general inventive concepts are described and illustrated herein in the context of various exemplary embodiments, these various aspects, concepts, and features may be used in many alternative embodiments, either individually or in various combinations and sub-combinations thereof. Unless expressly excluded herein, all such combinations and sub-combinations are intended to be within the scope of the general inventive concepts. Still further, while various alternative embodiments as to the various aspects, concepts, and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts, or features into additional embodiments and uses within the scope of the general inventive concepts even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary, or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated. Further, while disclosed benefits, advantages, and solutions to problems have been described with reference to specific embodiments, these are not intended to be construed as essential or necessary to the invention.

The invention claimed is:

1. A surgical guidance device (10) that comprises:
   a. a differential control assembly (50) that is cannulated for passage of a guidewire (15) therethrough, and aligned along a common axis with and within a housing (20), the differential control assembly (50) including a support shaft (51) having a proximally positioned drive connector (59) for engagement with a powered driving device (500), and a distally positioned tool connector (52) configured for attachment of a driver tool guide (200), a screw gear (53) and a chuck (54) that are releasably engagable to direct rotational movement of the screw gear (53) when the chuck (54) is engaged therewith, and a threaded carriage (55) translatable along the support shaft (51) for directing proximal or distal movement of the guidewire (15) through the differential control assembly (50), the threaded carriage (55) including at least one positive stop (57) which limits the proximal and distal translation of the carriage (55) within the housing (20), and
   b. an actuator assembly (29) including a handle (42) operably attached to a chuck mover (43) for actuating engagement of the chuck (54) with the screw gear (53), a directional actuator (30) for actuating movement of the carriage (55) proximally or distally, and a carriage lock (31) configured to releasably engage a thread guide (32) with the threaded carriage (55) wherein engagement thereof permits proximal or distal movement of the threaded carriage (55) along the support shaft (51) to effect proximal or distal movement of the guidewire (15),
   wherein the differential control assembly (50) is actuatable to first drive the guidewire (15) into a target site by engagement of the carriage lock (31) with the carriage (55) to direct distal movement of the guidewire (15), the depth thereof being governed by the at least one positive stop (57), and to differentially drive a screw affixed to the surgical guidance device (10) by actuating the handle (42) to engage the chuck (54) with the screw gear (53), and
   wherein the guidewire (15) is constructed from a material having sufficient column strength for penetrating a bone.

2. A surgical guidance device (10) comprising:
   a. a housing (20) having a proximal end (21), a center drive barrel (24), and a distal end (22), the proximal end (21) adapted with a hand grip (40) for gripping the surgical guidance device (10), the center drive barrel (24) configured to contain a differential control assembly (50) housed therein, the proximal end (21) of the housing (20) adapted for securing the housing (20) to a powered driving device (500),
   b. the differential control assembly (50) being cannulated for passage of a guidewire therethrough, and aligned along a common axis with and within the housing (20), the differential control assembly (50) including a support shaft (51) having a proximally positioned drive connector (59) for engagement with the powered driving device (500), and a distally positioned tool connector (52) configured for attachment of a driver tool guide (200), a screw gear (53) and a chuck (54) that are releasably engagable to direct rotational movement of the screw gear (53) when the chuck (54) is engaged therewith, a threaded carriage (55) translatable along the support shaft (51) for directing proximal or distal movement of the guidewire (15) through the differential control assembly (50), the threaded carriage (55) including at least one positive stop (57) which limits the proximal and distal translation of the carriage (55) within the housing (20), and
   c. an actuator assembly (29) including a hand grip (40) including a handle (42) operably attached to a chuck mover (43) for actuating engagement of the chuck (54) with the screw gear (53), a directional actuator (30) for actuating movement of the carriage (55) proximally or distally, and a carriage lock (31) configured to releasably engage a thread guide (32) with the threaded carriage (55) wherein engagement thereof permits proximal or distal movement of the threaded carriage (55 along the support shaft (51) to effect proximal or distal movement of the guidewire (15),
   wherein the differential control assembly (50) is actuatable to first drive the guidewire (15) into a target site by engagement of the carriage lock (31) with the carriage (55) to direct distal movement of the guidewire (15), the depth thereof being governed by the at least one positive stop (57), and to differentially drive a screw affixed to the surgical guidance device (10) by actuating the handle (42) to engage the chuck (54) with the screw gear (53), and wherein the directional actuator (30) is actuated to direct the guidewire (15) to move distally, and is released to retract the guidewire to move proximally, wherein displacement of the guidewire (15) is governed by the at least one positive stop (57), and wherein retraction of the guidewire (15) with the directional actuator (30) thereby differently permits distally directed driving of only the screw gear (53).

3. The surgical guidance device (10) according to claim 1 that includes a fixed grip (41).

4. The surgical guidance device (10) according to claim 1 wherein the driver tool (200) includes a drill guide.

5. The surgical guidance device (10) according to claim 1 wherein the differential control assembly (50) includes a connector (51) for securing to the powered driving device (500) and the powered driving device is a drill or power drill.

6. The surgical guidance device (10) according to claim 1 wherein the surgical guidance device (10) includes a trigger (70) for disengaging the screw gear (53) to stop rotation of a screw affixed to the surgical guidance device (10).

7. The surgical guidance device (10) according to claim 1 wherein surgical guidance device (10) includes a guidewire lock (71) for locking the guidewire in place to prevent one or more of its rotation, proximal translation, distal translation, or a combination thereof.

8. The surgical guidance device (10) according to claim 1 wherein the driver tool (200) is constructed to cooperate with a conjugately shaped portion of a screw and is adapted to receive passage of the guidewire therethrough.

9. The surgical guidance device (10) according to claim 1 wherein the directional actuator (30) is actuated to direct the guidewire (15) to move distally, and is released to retract the guidewire to move proximally, wherein displacement of the guidewire (15) is governed by the at least one positive stop (57), and wherein retraction of the guidewire (15) with the directional actuator (30) thereby differently permits distally directed driving of only the screw gear (53).

10. The surgical guidance device (10) according to claim 2 wherein the guidewire (15) is constructed from a material having sufficient column strength for penetrating a bone.

11. The surgical guidance device (10) according to claim 1 wherein the surgical guidance device (10) has a fixed length from proximal to distal wherein rotation and translation of the differential control assembly (50) occurs within the housing (20).

12. The surgical guidance device (10) according to claim 1 wherein a proximal end (20) of the housing (20) is integral with the powered driving device (500).

13. The surgical guidance device (10) according to claim 1 wherein the at least one positive stop is at least one ring that interferes within the housing to limit movement of the carriage (55).

14. The surgical guidance device (10) according to claim 1 wherein at least one positive stop includes two or more rings oriented proximally and distally relative to the carriage (55).

15. The surgical guidance device (10) according to claim 1 wherein the positive stop is a sleeve that encloses the carriage (55) to thereby limit its translation.

16. A method for directing sequentially a guidewire (15) and a screw into target bone by differentially directing the placement of a guidewire into bone and thereupon preventing further displacement of the guidewire (15) into bone and thereafter introducing the screw into bone, wherein the guidewire (15) is either maintained in place within the bone, or is withdrawn before or as the screw is inserted into the bone, the method employing a surgical guidance device (10) according to claim 1.

17. The surgical guidance device (10) according to claim 2 wherein the proximal end (20) of the housing (20) is integral with the powered driving device (500).

18. The surgical guidance device (10) according to claim 2 wherein the at least one positive stop is at least one ring that interferes within the housing to limit movement of the carriage (55).

19. The surgical guidance device (10) according to claim 2 wherein at least one positive stop includes two or more rings oriented proximally and distally relative to the carriage (55).

20. The surgical guidance device (10) according to claim 2 wherein the positive stop is a sleeve that encloses the carriage (55) to thereby limit its translation.

\* \* \* \* \*